(12) United States Patent
Wong

(10) Patent No.: US 12,345,619 B2
(45) Date of Patent: Jul. 1, 2025

(54) METHODS AND DEVICES FOR MINCING BIOLOGICAL TISSUE

(71) Applicant: GENETRACK BIOLABS INC., Vancouver (CA)

(72) Inventor: Edmond Tan-Loon Wong, Vancouver (CA)

(73) Assignee: GENETRACK BIOLABS INC., Vancouver (CA)

( * ) Notice: Subject to any disclaimer, the term of this patent is extended or adjusted under 35 U.S.C. 154(b) by 210 days.

(21) Appl. No.: 17/434,070

(22) PCT Filed: Jan. 20, 2021

(86) PCT No.: PCT/CA2021/050060
§ 371 (c)(1),
(2) Date: Aug. 26, 2021

(87) PCT Pub. No.: WO2021/146805
PCT Pub. Date: Jul. 29, 2021

(65) Prior Publication Data
US 2022/0349784 A1   Nov. 3, 2022

Related U.S. Application Data

(60) Provisional application No. 62/963,474, filed on Jan. 20, 2020.

(51) Int. Cl.
*G01N 1/28* (2006.01)

(52) U.S. Cl.
CPC ..... *G01N 1/286* (2013.01); *G01N 2001/2866* (2013.01)

(58) Field of Classification Search
CPC ........... G01N 1/286; G01N 2001/2866; G01N 2001/2873; C12M 45/02
See application file for complete search history.

(56) References Cited

U.S. PATENT DOCUMENTS

| 5,396,898 A | 3/1995 | Bittmann et al. |
| 5,731,199 A | 3/1998 | Roggero |
| 2001/0020655 A1 | 9/2001 | Vomhof et al. |
| 2011/0248105 A1 | 10/2011 | Braig et al. |
| 2013/0028813 A1 | 1/2013 | Shioyama et al. |

(Continued)

FOREIGN PATENT DOCUMENTS

| CN | 102217666 A | 10/2011 |
| CN | 102899241 A | 1/2013 |

(Continued)

OTHER PUBLICATIONS

International Patent Application No. PCT/CA2021/050060, International Search Report and Written Opinion dated Apr. 12, 2021.

(Continued)

*Primary Examiner* — Suman K Nath
(74) *Attorney, Agent, or Firm* — Borden Ladner Gervais LLP; Michael Damiani

(57) ABSTRACT

The specification describes devices, methods, and kits for mincing biological tissue. The method includes conforming biological tissue to having about uniform cross-sectional area planes along its length, and cutting the biological tissue. The conforming and cutting is performed cooperatively to control the size of the minced biological tissue. The device is suitable for use with the method.

27 Claims, 5 Drawing Sheets

(56) References Cited

U.S. PATENT DOCUMENTS

| | | | |
|---|---|---|---|
| 2015/0260615 A1* | 9/2015 | Turchi | G01N 1/08 |
| | | | 435/6.1 |
| 2018/0236457 A1 | 8/2018 | Graziano et al. | |
| 2019/0375125 A1* | 12/2019 | Schaser | B26D 1/54 |
| 2020/0072712 A1 | 3/2020 | Olson et al. | |

FOREIGN PATENT DOCUMENTS

| | | |
|---|---|---|
| CN | 110326695 A | 10/2019 |
| WO | 9823377 A1 | 6/1998 |
| WO | 2013070899 A1 | 5/2013 |
| WO | 2015163010 A1 | 10/2015 |

OTHER PUBLICATIONS

Canadian Patent Application No. 3,131,554, Office Action dated Jul. 4, 2022.

International Patent Application No. PCT/CA2021/050060, International Preliminary Report on Patentability dated Aug. 4, 2022.

Canadian Patent Application No. 3,131,554, Office Action dated Apr. 4, 2023.

European Patent Application No. 217451145, Extended European Search Report dated May 31, 2023.

Canadian Patent Application No. 3,131,554 Office Action dated Aug. 2, 2023.

Chinese Patent Application No. 202180002573.6, Office Action dated May 11, 2024. English Translation Available.

European Patent Application No. 217451145, European Office Action dated Mar. 5, 2024.

Canadian Patent Application No. 3,131,554, Canadian Office Action dated Apr. 18, 2024.

Chinese Patent Application No. CN202180002573.6 Office Action dated Dec. 4, 2024 English Translation Available.

European Patent Application No. 21745114.5 Summons to attent oral proceedings dated Apr. 8, 2025.

* cited by examiner

METHODS AND DEVICES FOR MINCING BIOLOGICAL TISSUE

FIELD

This invention relates to methods for mincing biological tissue and devices for performing them.

BACKGROUND

The following paragraphs are not an admission that anything discussed in them is prior art or part of the knowledge of persons skilled in the art.

Mincing biological tissue into sufficiently small fragments producing a sufficient quantity is required for multiple applications, for example, tissue preparation for flow cytometry, in vitro cell expansion, and cryopreservation.

INTRODUCTION

The following introduction is intended to introduce the reader to this specification but not to define any invention. One or more inventions may reside in a combination or sub-combination of the apparatus elements or method steps described below or in other parts of this document.

Processing a biological tissue sample is necessary in numerous therapeutic, diagnostic, medical, laboratory, and/or research applications. In one or more known biological tissue processing methods or devices, tissue samples are processed by mechanical disruption alone or in combination with chemical or enzymatic digestion. U.S. Pat. No. 7,270,284 teaches a biological tissue homogenizer that cuts tissue placed between two filters within a chamber. WO2016036464A1 teaches a device for dissociating a biological sample by pressing the biological tissue against stationary cutting blades configured in a planar orientation. EP2540394 discloses a device for fragmenting biological tissue by forcing the tissue, by rotation of a helically shaped transportation element, past processing tools comprising teeth-like structures. WO2015161057 teaches a biological tissue mincing tool comprising two generally aligned mincer screens that are moved through a tissue sample to mince the tissue, and a wiper configured for wiping minced tissue off the distal side of the second mincer screen. The inventors have identified that one or more known biological tissue processing methods or devices do not produce biological tissue fragments: 1) of a desired size with sufficient consistency; 2) at a sufficiently large volume over a sufficiently short time period; 3) using a process that is consistent and/or compatible with automation and/or industrial scaling; or 4) any combination thereof.

Generating biological tissue fragments having a desired size is important for cell therapy applications, for example, cell immunotherapy including immunomodulation and cancer therapy; cell based replacement or regeneration application for treatment of degenerative disease, surgery and tissue engineering; and gene therapy. Generating a sufficiently large volume or quantity of biological tissue fragments over a sufficiently short time period is important in producing cellular therapy products in sufficient volume for clinical trial studies, manufacturing, and for reducing repetitive workload in experiments. Improving consistency of and being able to define tissue fragment size may be important in ensuring consistent quality of starting product for manufacturing, particularly ensuring consistent surface area-to-volume ratio in subsequent processing steps, including but not limited to proteolysis, gene transfection, and cryopreservant, Generating a sufficiently large volume of biological tissue fragments over a sufficiently short time period is also important in reducing operational costs.

The inventors have discovered that by coupling and controlling: 1) the velocity at which biological tissue is conformed to having about uniform cross-sectional area planes along its length; and 2) the frequency at which the biological tissue is cut to a desired length, allows for producing a biological tissue fragment of a desired size with sufficient or optimized consistency, and/or at a sufficiently large volume over a sufficiently short time period. The velocity and frequency are selected to produce a desired amount of biological tissue fragments having a desired biological tissue fragment size over a desired period of time.

This specification describes a method for mincing biological tissue, the method comprising: conforming biological tissue to having about uniform cross-sectional area planes along its length; and cutting the biological tissue, where the conforming and cutting are performed cooperatively to control the size of the minced biological tissue.

Optionally, the conforming and cutting are performed cooperatively to control the size of the minced tissue the using the following equation:

$$\text{Minced Tissue Size(e.g. minced tissue volume)} = \frac{\text{Velocity of tissue in diretion of mincing} \times \text{cross-sectional area of conformed tissue}}{\text{Cutting Frequency}}.$$

The biological tissue may be epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof.

The cutting may be performed on conformed tissue. The cutting may be actuated from the cutting side of the tissue.

The conforming may be performed on unminced tissue or partly minced tissue. The cutting may be performed along a plane that is about perpendicular to the length of the tissue. The cutting may be performed on the entirety of the tissue along a cutting plane. The cutting may be performed at a distance of from about 0 cm to about 10 cm from the conforming, or abutting the conforming.

The cutting may be performed by a movable cutter. The moveable cutter may be a rotating cutter, a linear-motion guillotine cutter, vibrating cutter, ultrasonic cutter, waterjet cutter, a cutter that moves linearly, an oscillating blade including a serrated blade with or without an opposing fixed or counteracting blade, a plate, or laser cutter.

The conforming may be performed by feeding tissue through at least one hole defined by a conforming plate. Optionally, the conforming and cutting may be performed cooperatively to control the size of the minced tissue the using the following equation:

$$\text{Minced Tissue Size(e.g. minced tissue volume)} = \frac{\text{Velocity of tissue through the at least one hole} \times \text{cross-sectional area of the at least one hole}}{\text{Cutting Frequency}}.$$

Optionally, the conforming plate may comprise two or more holes having about uniform cross-sectional areas, and the conforming and cutting may be performed cooperatively to control the size of the minced tissue the using the following equation:

$$\text{Minced Tissue Size(e.g. minced tissue volume)} = \frac{\text{Velocity of tissue through the at least one hole} \times \text{cross-sectional area of the at least one hole}}{\text{Cutting Frequency} \times n(\text{number of holes})}.$$

The conforming and/or the cutting may be automated. The conforming and cutting may be performed cooperatively by a processor configured to control the size of the minced tissue.

The conforming may produce conformed tissue(s) having a cross-sectional area of from about 0.1 mm$^2$ to about 50 mm$^2$. The herein disclosed method may comprise conforming and/or cutting from about 1 to about 100,000 tissues at the same time. The conformed tissues may have about uniform cross-sectional areas.

The specification also describes a device for mincing biological tissue, the device comprising: a conforming plate defining at least one hole therethrough and having a loading side and an opposite emerging side, the conforming plate coupleable on the loading side with a tissue feeder to feed tissue through the at least one hole; and a cutter configured to cut the biological tissue, where the tissue feeder and the cutter cooperate to control the size of the minced biological tissue.

Optionally, the tissue feeder and the cutter cooperate to control the size of the minced tissue using the following equation:

$$\text{Minced Tissue Size(e.g. minced tissue volume)} = \frac{\text{Velocity of tissue in \textit{diretion} of mincing} \times \text{cross-sectional area of conformed tissue}}{\text{Cutting Frequency}}.$$

Optionally, the tissue feeder and the cutter cooperate to control the size of the minced tissue using the following equation:

$$\text{Minced Tissue Size (e.g. minced tissue volume)} = \frac{\text{Velocity of tissue through the at least one hole} \times \text{cross-sectional area of the at least one hole}}{\text{Cutting Frequency}}$$

Optionally, the herein disclosed device comprises two or more holes having about uniform cross-sectional areas, wherein the tissue feeder and the cutter cooperate to control the size of the minced tissue using the following equation:

$$\text{Minced Tissue Size(e.g. minced tissue volume)} = \frac{\text{Velocity of tissue through the at least one hole} \times \text{cross-sectional area of the at least one hole}}{\text{Cutting Frequency} \times n(\text{number of holes})}.$$

The biological tissue may be epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof.

The cutter may be on the emerging side of the conforming plate.

The tissue fed through the at least one hole may be unminced or partly minced tissue.

The cutter may be from about 0 cm to about 10 cm from the conforming plate, or abutting the conforming plate. The cutter may be a movable cutter. The movable cutter may be a rotating cutter, a linear-motion guillotine cutter, vibrating cutter, ultrasonic cutter, waterjet cutter, a cutter that moves linearly, an oscillating blade including a serrated blade with or without an opposing fixed or counteracting blade, a plate, or laser cutter. The movable cutter may be actuated from the emerging side of the conforming plate.

The cutter may be configured to cut the tissue along a plane that is about perpendicular to the direction of the tissue being fed through the at least one hole. The cutter may be configured to cut the tissue entirely along a cutting plane. The edge of the conforming plate defining the at least one hole may be dull.

The tissue feeder may comprise a chamber. The chamber may comprise a member, for example a plunger, movable within the chamber, the member configured for forcing the tissue through the at least one hole.

The tissue feeder and/or the cutter may be automated. The tissue feeder and/or the cutter may be in communication with a processor configured to control the size of the minced tissue.

The at least one hole may have an area of from about 0.1 mm$^2$ to about 50 mm$^2$. The conforming plate may define from 1 to 100,000 holes therethrough.

The herein disclosed device for mincing biological tissue may be made of material suitable for biomedical use, autoclavable, sterile, or any combination thereof.

The herein disclosed device for mincing biological tissue is believed to be particularly suitable for use with the method described above.

The specification further describes a biological tissue mincing device for use with at least two actuators, the device comprising: a conforming plate defining at least one hole therethrough and having a loading side and an opposite emerging side, the conforming plate coupleable on the loading side with a chamber to hold and feed tissue through the at least one hole; and a cutter configured to cut the tissue, where the chamber is cooperatively associated with the cutter to control the size of the minced biological tissue, and where the chamber is coupleable with one of the at least two actuators, and where the cutter is coupleable with another of the at least two actuators.

The one actuator may co-act with the chamber and the another may actuator co-act with the cutter to control the size of the minced tissue.

Optionally, the herein disclosed biological tissue mincing device is coupleable to a processor configured to control the size of the minced tissue using the following equation:

Minced Tissue Size(e.g. minced tissue volume) =

$$\frac{\text{Velocity of tissue in } \textit{diretion} \text{ of mincing} \times \text{cross-sectional area of conformed tissue}}{\text{Cutting Frequency}}.$$

Optionally, the herein disclosed biological tissue mincing device is coupleable to a processor configured to control the size of the minced tissue using the following equation:

Minced Tissue Size(e.g. minced tissue volume) =

$$\frac{\text{Velocity of tissue through the at least one hole} \times \text{cross-sectional area of the at least one hole}}{\text{Cutting Frequency}}.$$

Optionally, the herein disclosed biological tissue mincing device comprises two or more holes having about uniform cross-sectional area, wherein the device is coupleable to a processor configured to control the size of the minced tissue using the following equation:

Minced Tissue Size(e.g. minced tissue volume) =

$$\frac{\text{Velocity of tissue through the at least one hole} \times \text{cross-sectional area of the at least one hole}}{\text{Cutting Frequency} \times n(\text{number of holes})}.$$

The tissue may be biological tissue, such as epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof.

The cutter may be on the emerging side of the conforming plate. The cutter may be coupleable with the another actuator on the emerging side of the conforming plate.

The tissue fed through the at least one hole may be unminced or partly minced tissue.

The cutter may be from about 0 cm to about 10 cm from the conforming plate, or abutting the conforming plate. The cutter may be a movable cutter. The movable cutter may be a rotating cutter, a linear-motion guillotine cutter, vibrating cutter, ultrasonic cutter, waterjet cutter, a cutter that moves linearly, an oscillating blade including a serrated blade with or without an opposing fixed or counteracting blade, a plate, or laser cutter. The cutter may be configured to cut the tissue along a plane that is about perpendicular to the direction of the tissue being fed through the at least one hole. The cutter may be configured to cut the tissue entirely along a cutting plane. The edge of the conforming plate defining the at least one hole may be dull.

The chamber may be coupleable with a member, for example a plunger, movable within the chamber, the member configured for forcing the tissue through the at least one hole.

The tissue feeder and/or the cutter may be automated. The at least one hole may have an area of from about 0.1 mm² to about 50 mm². The conforming plate may define from 1 to 100,000 holes therethrough.

The herein disclosed biological tissue mincing device may be made of material suitable for biomedical use, autoclavable, sterile, or any combination thereof.

The herein disclosed biological tissue mincing device is believed to be particularly suitable for use with the method described above.

The specification further describes a kit comprising: a chamber; a conforming plate defining at least one hole therethrough and having a loading side and an opposite emerging side, the conforming plate coupleable on the loading side with the chamber to hold and feed biological tissue through the at least one hole; and a cutter, where the chamber is cooperatively associated with the cutter to control the size of minced biological tissue.

In at least some cases, the methods and devices disclosed herein may reduce the operating cost compared to similar biological tissue mincing methods or devices that do not couple and control the velocity at which biological tissue is conformed to having about uniform cross-sectional area planes along its length, and the frequency at which the biological tissue is cut to a desired length, by, for example, producing more desirable biological tissue fragments over a shorter period of time, producing less undesirable or unusable biological tissue fragments, making the methods and devices more amenable and/or compatible to automation, reducing hand-on time, and/or increasing predictability and uniformity of tissue fragment size. Without intending to be limited by theory, coupling the velocity at which biological tissue is conformed to having about uniform cross-sectional area planes along its length, and the frequency at which the biological tissue is cut to a desired length requires less energy to operate than independently operating the velocity and frequency.

BRIEF DESCRIPTION OF THE DRAWINGS

Embodiments of the present disclosure will now be described, by way of example only, with reference to the attached FIGS.

DETAILED DESCRIPTION

Figure 1:
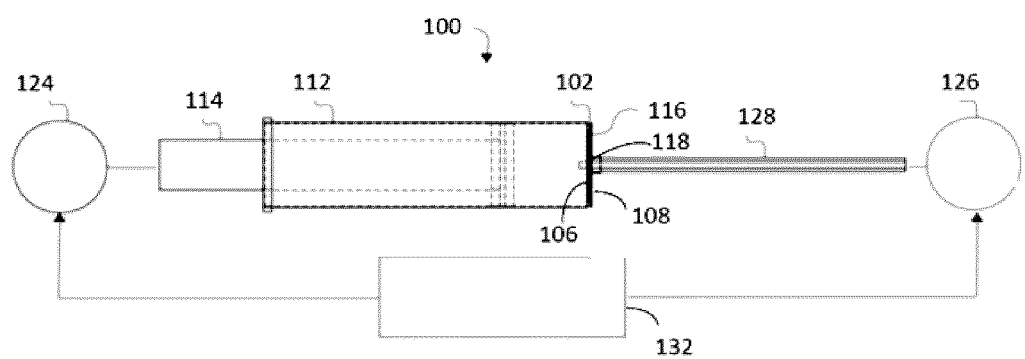
FIG. 1 is an illustration of one example of a herein disclosed mincing device.

The specification describes a method for mincing biological tissue. The method includes conforming biological tissue to having about uniform cross-sectional area planes along its length, and cutting the biological tissue. The conforming and cutting is performed cooperatively to control the size of the minced biological tissue.

The specification also describes a device for mincing biological tissue. The device includes a conforming plate defining at least one hole therethrough and having a loading side and an opposite emerging side. The conforming plate is coupleable on the loading side with a tissue feeder to feed tissue through the at least one hole. The device also includes a cutter configured to cut the tissue. The tissue feeder and the cutter cooperate to control the size of the minced biological tissue.

The specification also describes a biological tissue mincing device for use with at least two actuators. The device includes a conforming plate defining at least one hole therethrough and having a loading side and an opposite emerging side. The conforming plate is coupleable on the loading side with a chamber to hold and feed biological tissue through the at least one hole. The tissue mincing device also includes a cutter configured to cut the biological tissue. The chamber is cooperatively associated with the cutter to control the size of the minced biological tissue, and the chamber is coupleable with one of the at least two actuators. The cutter is coupleable with another of the at least two actuators.

In the context of the present disclosure, biological tissue refers to any collection of interconnected cells, for example epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof. Biological tissue can be obtained from in vivo sources, such as a human, animal, or plant subject, or from in vitro sources, such as laboratory grown, engineered, or cultured tissue. Mincing tissue refers to dissociating, breaking, and/or separating biological tissue into one or more tissue fragments. Biological tissue fragments are considered to be dissociated, broken, and/or separated from the biological tissue when they are able to freely move independent of the biological tissue.

The number of fragments of biological tissue produced by the herein disclosed methods and devices may vary and be adjusted depending on: 1) the desired size, shape, and/or quantity of minced biological tissue; 2) the type of the biological tissue; 3) the ability to feed biological tissue for conforming and/or cutting, which is described in more detail below; or 4) any combination thereof. The herein disclosed methods and devices may cause biological tissue to be minced into 1 or more fragments, for example, 2 or more fragments, 3 or more fragments, 4 or more fragments, 5 or more fragments, 6 or more fragments, 7 or more fragments, 8 or more fragments, 9 or more fragments, 10 or more fragments, 15 or more fragments, 20 or more fragments, 25 or more fragments, 50 or more fragments, 75 or more fragments, 100 or more fragments, 1000 or more fragments, 10,000 or more fragments, 100,000 or more fragments, 1,000,000 or more fragments, or 1,000,000,000 or more fragments. In some examples, the herein disclosed methods and devices may cause biological tissue to be minced into 1,000,000,000 tissue fragments when implemented on an industrial manufacturing scale.

The size of biological tissue for mincing and the number of biological tissue samples for mincing, by the herein disclosed methods and devices, may vary and be adjusted depending on: 1) the desired size, shape, and/or quantity of minced biological tissue; 2) the type of the biological tissue; 3) the ability to feed biological tissue for conforming and/or cutting, which is described in more detail below; or 4) any combination thereof. There herein disclosed methods and devices may mince 1 or more biological tissue samples, 2 or more biological tissue samples, 3 or more biological tissue samples, 4 or more biological tissue samples, 5 or more biological tissue samples, 10 or more biological tissue samples, or 100 or fewer biological tissue samples. The 2 or more biological tissue samples may be the same tissue type or may be different types of tissue. The 2 or more biological tissue samples may be minced sequentially or in parallel, which is described in more detail below. The herein disclosed methods and devices may mince biological tissue having a size from about 1 mm$^3$ to about 2000 cm$^3$, for example about 20 mm$^3$ or the size of a small biopsy. The size of the biological tissue samples for mincing may be limited by the limitations of feeding the sample for mincing.

Conforming biological tissue refers to causing the tissue to have about uniform cross-sectional area planes along its length, which may result in an outer surface layer of tissue being removed and/or shaved from none, one or more portions of, or along the entire length of the tissue being conformed. Conforming biological tissue is performed beginning from, or close to, one end of the tissue and proceeds along the tissue's axis of conformation towards an opposite end of the tissue thereby defining a direction of mincing. The axis of conformation refers to the length of the tissue. After processing, cross-sectional area planes of the tissue, which refers to any plane that intersects the tissue at a right angle to the axis of conformation, have about uniformed sized areas along their length, for example, greater than about 60% uniformity, greater than about 70% uniformity, greater than about 75% uniformity, greater than about 80% uniformity, greater than about 85% uniformity, greater than about 90% uniformity, greater than about 95% uniformity, or about 100% uniformity.

The amount and location of tissue removed during conforming by the herein disclosed methods and devices may vary and be adjusted depending on: 1) the desired size, shape, and/or quantity of minced biological tissue; 2) the type of biological tissue; 3) the size and/or shape of the pre-conformed tissue; or 4) any combination thereof. Optionally, during conforming, some tissue may be removed at one portion along the length of the biological tissue while at another portion along the length of the biological tissue, a greater, a lesser, or no amount of tissue is removed. Optionally, the removing and/or shaving of tissue during conforming may be performed on all sides along the length of the biological tissue or fewer than all sides along the length of the biological tissue, for example, on one side along the length of the biological tissue. Optionally, the removing and/or shaving is performed on a portion of a side of the biological tissue, for example, a portion of the perimeter of a cross-sectional plane along the length of the biological tissue. The portion of the perimeter may be at least about 5%, at least about 10%, at least about 25%, at least about 50%, at least about 90%, at least about 95%, or 100% of a cross-sectional plane along the length of the biological tissue.

The cross-sectional area of the conformed tissue conformed by the herein disclosed methods and devices may vary and be adjusted depending on: 1) the desired size, shape, and/or quantity of minced biological tissue; 2) the type of biological tissue; 3) the size and/or shape of the pre-conformed tissue; or 4) any combination thereof. Tissue conformed by the herein disclosed methods and devices may have a cross-sectional area of from about 0.1 mm$^2$ to about 10,000 mm$^2$, for example, from about 0.1 mm$^2$ to about 20 mm$^2$, from about 0.1 mm$^2$ to about 10 mm$^2$, about 0.1 mm$^2$, about 0.2 mm$^2$, about 0.3 mm$^2$, about 0.4 mm$^2$, about 0.5 mm$^2$, about 0.6 mm$^2$, about 0.7 mm$^2$, about 0.8 mm$^2$, about 0.9 mm$^2$, about 1.0 mm$^2$, about 2.0 mm$^2$, about 3.0 mm$^2$, about 4.0 mm$^2$, about 5.0 mm$^2$, about 10 mm$^2$, about 15 mm$^2$, about 20 mm$^2$, about 50 mm$^2$, about 100 mm$^2$, about 1,000 mm$^2$, about 10,000 mm$^2$, or from any one of the above stated areas to any other above stated areas. In some examples, the cross-sectional area is only limited by the limitations of feeding tissue for conforming.

The herein disclosed methods and devices may conform 1 or more biological tissues in parallel or in series. Optionally, one or more biological tissues may be conformed into 1 or more conformed tissues, for example, a biological tissue may be conformed into 1 or more conformed tissues, 2 or more conformed tissues, 3 or more conformed tissues, 4 or more conformed tissues, 5 or more conformed tissues, 6 or more conformed tissues, 7 or more conformed tissues, 8 or more conformed tissues, 9 or more conformed tissues, 10 or more conformed tissues, 11 or more conformed tissues, 12 or more conformed tissues, 13 or more conformed tissues, 14 or more conformed tissues, 15 or more conformed tissues, 16 or more conformed tissues, 17 or more conformed tissues, 18 or more conformed tissues, 19 or more conformed tissues, 20 or more conformed tissues, 30 or more conformed tissues, 40 or more conformed tissues, 50 or more conformed tissues, 60 or more conformed tissues, 70 or more conformed tissues, 80 or more conformed tissues, 90 or more conformed tissues, 100 or more conformed tissues, 125 or more conformed tissues, 150 or more conformed tissues, 200 or more conformed tissues, 250 or more conformed tissues, 300 or more conformed tissues, 350 or more conformed tissues, 400 or more conformed tissues, 450 or more conformed tissues, 500 or more conformed tissues, 600 or more conformed tissues, 700 or more conformed tissues, 800 or more conformed tissues, 900 or more conformed tissues, 1,000 or more conformed tissues, 5,000 or more conformed tissues, 10,000 or more conformed tissues, 100,000 or more conformed tissues, 300,000 or more conformed tissues, or 1,000,000 or fewer conformed tissues, in parallel. When 2 or more biological tissues are being conformed in parallel, each of the 2 or more conformed tissues may have the same or different cross-sectional areas. Conformed tissue may be entirely dissociated, broken, and/or separated from the pre-conformed biological tissue, or an end portion of the conformed tissue may be associated, connected, and/or joined to the pre-conformed biological tissue.

The size of the conformed tissue conformed by the herein disclosed methods and devices may vary and be adjusted depending on: 1) the desired size, shape, and/or quantity of minced biological tissue; 2) the type of biological tissue; 3) the size and/or shape of the pre-conformed tissue; or 4) any combination thereof. For example, to produce minced biological tissue having a desired size and/or shape, the size of conformed tissue produced by the herein disclosed methods and devices using pre-cut biological tissue may differ from the size of conformed tissue produced by the herein disclosed methods and devices using post-cut biological tissue.

The velocity at which tissue is conformed along the direction of mincing by the herein disclosed methods and devices may vary and be adjusted depending on: 1) the desired size, shape, and/or quantity of minced biological tissue; 2) the type of biological tissue; 3) the size and/or shape of the pre-conformed tissue; or 4) any combination thereof, which will be described in more detail below. Velocity at which tissue is conformed along the direction of mincing by the herein disclosed methods and devices may be from about 0.1 cm/second to about 1,000 cm/second, for example, about 0.1 cm/second, 0.5 cm/second, 1.0 cm/second, 5.0 cm/second, 10 cm/second, 25 cm/second, 50 cm/second, 100 cm/second, 500 cm/second 1,000 cm/second, or from any one of the above stated velocities to any other above stated velocities.

Cutting tissue refers to causing a portion of the tissue to become dissociated, broken, and/or separated from the pre-dissociated, pre-broken, and/or pre-separated tissue. The number of cut tissues produced by the herein disclosed methods and devices may vary and be adjusted depending on: 1) the desired size, shape, and/or quantity of minced biological tissue; 2) the type of biological tissue; 3) the size and/or shape of the pre-cut tissue; or 4) any combination thereof. The herein disclosed methods and devices may cut one or more biological tissues into 1 or more cut tissues in parallel or in series, for example, into 1 or more cut tissues, 2 or more cut tissues, 3 or more cut tissues, 4 or more cut tissues, 5 or more cut tissues, 6 or more cut tissues, 7 or more cut tissues, 8 or more cut tissues, 9 or more conformed tissues, 10 or more cut tissues, 11 or more cut tissues, 12 or more cut tissues, 13 or more cut tissues, 14 or more cut tissues, 15 or more cut tissues, 16 or more cut tissues, 17 or more cut tissues, 18 or more cut tissues, 19 or more cut tissues, 20 or more cut tissues, 30 or more cut tissues, 40 or more cut tissues, 50 or more cut tissues, 60 or more cut tissues, 70 or more cut tissues, 80 or more cut tissues, 90 or more cut tissues, 100 or more cut tissues, 125 or more cut tissues, 150 or more cut tissues, 200 or more cut tissues, 250 or more cut tissues, 300 or more cut tissues, 350 or more cut tissues, 400 or more cut tissues, 450 or more cut tissues, 500 or more cut tissues, 600 or more cut tissues, 700 or more conformed tissues, 800 or more cut tissues, 900 or more cut tissues, 1,000 or more cut tissues, 10,000 or more cut tissues, 100,000 or more cut tissues, 300,000 or more cut tissues, or 1,000,000 or fewer cut tissues. In one example, a placenta having a volume of about 300 cc may be cut into about 300,000 tissue fragments each having a size of about 1 mm$^2$.

The size of the cut tissue produced by the herein disclosed methods and devices may vary and be adjusted depending on: 1) the desired size, shape, and/or quantity of minced biological tissue; 2) the type of biological tissue; 3) the size and/or shape of the pre-cut tissue; or 4) any combination thereof. For example, to produce minced biological tissue having a desired size and/or shape, the size of cut tissue produced by the herein disclosed methods and devices using pre-conformed biological tissue may differ from the size of cut tissue produced by the herein disclosed methods and devices using post-conformed biological tissue.

The velocity at which biological tissue is fed along the direction of mincing for cutting and the frequency at which the tissue is cut by the herein disclosed methods and devices may vary and be adjusted depending on: 1) the desired size, shape, and/or quantity of minced biological tissue; 2) the type of biological tissue; 3) the size and/or shape of the pre-cut tissue; or 4) any combination thereof, which will be described in more detail below. Velocity at which tissue is fed for cutting along the direction of mincing by the herein disclosed methods and devices may be from about 0.1 cm/second to about 1,000 cm/second, for example, about 0.1 cm/second, 0.5 cm/second, 1.0 cm/second, 5.0 cm/second, 10 cm/second, 25 cm/second, 50 cm/second, 100 cm/second, 500 cm/second 1,000 cm/second, or from any one of the above stated velocities to any other above stated velocities. Optionally, the velocity at which tissue is fed for cutting along the direction of mincing by the herein disclosed methods and devices is about equal or equal to the herein disclosed velocity at which tissue is conformed along the direction of mincing. Frequency of cutting by the herein disclosed methods and devices may be from about 0.1 Hz to about 500 Hz, for example, about 0.1 Hz, about 0.5 Hz, about 1.0 Hz, about 5.0 Hz, about 10 Hz, about 25 Hz, about 50 Hz, about 100 Hz, about 120 Hz, about 150 Hz, about 250 Hz, about 500 Hz, or from any one of the above stated frequencies to any other above stated frequencies.

The herein disclosed methods and devices may cut: 1) conformed tissue; 2) pre-conformed tissue; 3) tissue while it is being conformed; and/or 4) cut tissue. Cutting pre-conformed tissue may be used when, for example, it is desirable to increase the number of disposal options. Cutting conformed tissue may be used when, for example, it is desirable to decrease the complexity of device design. The proximity of the herein disclosed cutting and the herein disclosed conforming may vary and be adjusted depending on: 1) the desired size, shape, and/or quantity of minced biological tissue; 2) the type of biological tissue; or 3) a combination thereof. The herein disclosed proximity may be a distance from about 0 cm to about 10 cm, for example, about 0 cm, about 0.1 cm, about 0.2 cm, about 0.3 cm, about 0.4 cm, about 0.5 cm, about 0.6 cm, about 0.7 cm, about 0.8 cm, about 0.9 cm, about 1.0 cm, about 1.5 cm, about 2.0 cm, about 5.0 cm, about 7.0 cm, about 10 cm, or from any one of the above stated distances to any other above stated distances, or the herein disclosed cutting and the herein disclosed conforming directly abut one another, i.e., are in direct contact with one another. Optionally, a cut tissue is cut one or more additional times.

Cutting may be performed along any plane angle that causes a portion of tissue to become dissociated, broken, and/or separated from the pre-dissociated, pre-broken, and/or pre-separated tissue. The herein disclosed cutting may be performed along a plane that intersects the axis of conformation at an angle from about 5° to about 175°, for example, about 5°; about 10°; about 20°; about 30°; about 40°; about 50°; about 60°; about 70°; about 80°; about 90°; about 100°; about 110°; about 120°; about 130°; about 140°; about 150°; about 160°; about 170°; about 175°; or the angle is from any one of the listed angles to any other of the listed angles. In some examples, the cutting plane is perpendicular to the length of the tissue being cut. A skilled person would understand that in embodiments where pre-conformed tissue is cut, the axis of conformation refers to the axis along which the cut tissue is conformed following cutting.

The herein disclosed conforming and cutting are performed cooperatively to control the size of the minced tissue. Cooperatively refers to adjusting the herein disclosed parameters of conforming in view of one or more of the herein disclosed parameters of cutting, and adjusting the herein disclosed parameters of cutting in view of one or more of the herein disclosed parameters of conforming, to produce minced tissue having a desired size and/or desired quantity of minced tissue fragments. Examples of the herein disclosed parameters of conforming and cutting include: cross-sectional area planes of conformed biological tissue(s); number of conformed biological tissues produced in series or in parallel; velocity at which biological tissue is conformed; cross-sectional area of conformed tissue; number of cut tissues produced in series or in parallel; velocity at which biological tissue is fed for cutting; frequency of cutting; proximity of conforming and cutting; angle of cutting; and alignment of conforming and cutting. Optionally, the conforming and cutting are performed cooperatively to control the size of minced tissue using Equation 1:

$$\text{Minced Tissue Size(e.g. minced tissue volume)} = \frac{\text{Velocity of tissue in } \textit{diretion} \text{ of mincing} \times \text{cross-sectional area of conformed tissue}}{\text{Cutting Frequency}}.$$

(Equation 1)

With reference to Equation 1, the herein disclosed parameters of velocity of biological tissue along the direction of mincing for conforming and cutting, the cross-sectional area of the conformed tissue, and the cutting frequency are adjustable to result in minced tissue having a desired size. The herein disclosed methods and devices may mince biological tissue into tissue fragments having a size of from about 0.001 mm³ to about 100,000 mm³, for example, about 0.001 mm³, about 0.005 mm³, about 0.01 mm³, about 0.1 mm³, about 1.0 mm³, about 10 mm³, about 50 mm³, about 100 mm³, about 150 mm³, about 200 mm³, about 300 mm³, about 350 mm³, about 400 mm³, about 500 mm³, about 1,000 mm³, about 10,000 mm³, about 100,000 mm³, or from any one of the above stated sizes to any other above stated sizes.

The herein disclosed conforming and/or cutting may be automated to produce minced tissue fragments of desired size(s) and/or a desired quantity of minced tissue fragments. One or more of the herein disclosed conforming parameters and/or one or more of the herein disclosed cutting parameters may be automatically adjusted based on the resulting desired size(s) of minced tissue fragments. Based on the desired size(s) of minced tissue fragments, the automation may also adjust one or more of the herein disclosed conforming parameters and/or one or more of the herein disclosed cutting parameters to result in a desired quantity of minced tissue fragments. The automation may be computer based, mechanical based, or a combination thereof. For example, a user may enter or set the desired minced tissue fragment size or sizes and the herein disclosed conforming and/or cutting automatically adjust one or more parameters to result in the desired minced tissue fragment size. Optionally, the user may enter or set the desired quantity of minced tissue fragments and the desired tissue fragment size(s), and the herein disclosed conforming and/or cutting automatically adjust one or more parameters to result in the desired tissue quantity.

The herein disclosed conforming may be performed by feeding biological tissue through at least one hole defined by a plate, which is referred to herein as a conforming plate. The plate is configured such that passing biological tissue through at least one hole of the plate causes the biological tissue to have cross-sectional planes along its length that are about the same area as the area of the at least one hole. The biological tissue may be fed in the direction of mincing through the at least one hole of the plate from either side of the plate, the sides of the plate being about perpendicular to the direction of mincing. As herein disclosed, the side of the plate from which the biological tissue is fed may be referred to as the loading side and the opposite side of the plate may be referred to as the emerging side. Optionally, the loading side and the emerging side of the plate have a planar orientation.

The number, size, and shape of the holes defined by the herein disclosed plate may vary and be adjusted depending on: 1) the desired size, shape, and/or quantity of minced biological tissue; 2) the type of biological tissue; 3) the size and/or shape of the pre-conformed tissue; or 4) any combination thereof. The plate may define 1 or more holes, 2 or more holes, 3 or more holes, 4 or more holes, 5 or more holes, 6 or more holes, 7 or more holes, 8 or more holes, 9 or more holes, 10 or more holes, 11 or more holes, 12 or more holes, 13 or more holes, 14 or more holes, 15 or more holes, 16 or more holes, 17 or more holes, 18 or more holes, 19 or more holes, 20 or more holes, 30 or more holes, 40 or more holes, 50 or more holes, 60 or more holes, 70 or more holes, 80 or more holes, 90 or more holes, 100 or more holes, 125 or more holes, 150 or more holes, 200 or more holes, 250 or more holes, 300 or more holes, 350 or more holes, 400 or more holes, 450 or more holes, 500 or more holes, 600 or more holes, 700 or more holes, 800 or more holes, 900 or more holes, 1,000 or more holes, 5,000 or more holes, 10,000 or more holes, 50,000 or more holes, 100,000 or more holes, 500,000 or more holes, 1,000,000 or more holes, 10,000,000 or more holes, 50,000,000 or more holes, 1,000,000,000 or more holes, or from any one of the above stated number of holes to any other above stated number of holes. In an example, the herein disclosed plate has a cross sectional area of about 10 cm$^2$ and defines about 50,000 holes each having a diameter of about 0.5 mm.

Each of the one or more holes defined by the herein disclosed plate may have an area of from about 0.1 mm$^2$ to about 10,000 mm$^2$, for example, from about 0.1 mm$^2$ to about 20 mm$^2$, from about 0.1 mm$^2$ to about 10 mm$^2$, about 0.1 mm$^2$, about 0.2 mm$^2$, about 0.3 mm$^2$, about 0.4 mm$^2$, about 0.5 mm$^2$, about 0.6 mm$^2$, about 0.7 mm$^2$, about 0.8 mm$^2$, about 0.9 mm$^2$, about 1.0 mm$^2$, about 2.0 mm$^2$, about 3.0 mm$^2$, about 4.0 mm$^2$, about 5.0 mm$^2$, about 10 mm$^2$, about 15 mm$^2$, about 20 mm$^2$, about 50 mm$^2$, about 100 mm$^2$, about 1,000 mm$^2$, about 10,000 mm$^2$, or from any one of the above stated areas to any other above stated areas. When the herein disclosed plate defines two or more holes, each of the two or more holes may have the same area or a different area from one or more other holes defined by the plate. Each of the one or more holes may have any desired shape, for example, square, rectangle, trapezoid, triangle, hexagon, octagon, circle, or oval. When the herein disclosed plate defines two or more holes, each of the two or more holes may have the same shape or a different shape from one or more other holes defined by the plate. The number, size, and shape of the holes defined by the herein disclosed plate may be adjustable by, for example, moving a portion of the plate or a second plate adjacent to the plate, to adjust the cross-sectional area of one or more holes. Optionally, the number, size, and shape of the holes may be adjusted by replacing a herein disclosed plate with another herein disclosed plate defining a different number, size, and/or shape of holes. Optionally, the edge of the conforming plate that defines the one or more holes of the herein disclosed plate may be dull such that during conforming, the tissue is not cut as disclosed herein.

Feeding biological tissue through at least one hole defined by a plate may be performed by a chamber attached to the plate and having a member, for example a plunger, movable within the chamber. Biological tissue within the chamber may be moved or forced towards and through the at least one hole of the plate by a pushing force exerted on the tissue by the member. The herein disclosed chamber may adjust the velocity at which the biological tissue is fed through the at least one hole defined by the herein disclosed plate or the velocity at which the tissue is conformed, by adjusting the velocity at which the member pushes biological tissue through the at least one hole. Optionally, the inner wall of the chamber comprises one or more notches or protrusions that limit the movability of the member within the chamber. For example, the inner wall of the chamber may comprise a protrusion proximal to the loading side of the herein disclosed plate that prevents the member from sliding past the protrusion in the direction of the plate.

The plate may be attached at any position along the chamber provided that the biological tissue may be fed along the direction of mincing through the at least one hole of the plate. In some embodiments, the plate is attached at or near the end of the chamber. The chamber being attached to the plate refers to any attachment that is coupleable, permanent, or semi-permanent. The term "coupleable" refers to being releasably attached, for example, the chamber can be freely detached from and re-attached to the plate. Any suitable fastener may be used to couple the chamber and plate, for example, latches, hook and loop, notches, grooves, pins, tethers, hinges, non-permanent adhesives, and combinations thereof. In some embodiments, the chamber has a threaded wall that is configured to be screw threaded with the plate. In other embodiments, the chamber has a perimeter portion defining one or more latches configured to releasably engage with one or more grooves or recesses formed from a rim portion of the plate. Optionally, the chamber and plate may be attached permanently or semi-permanently by a permanent adhesive, a semi-permanent adhesive, a weld, or a solder.

The size and shape of the herein disclosed chamber may vary and be adjusted depending on: 1) the desired size, shape, and/or quantity of minced biological tissue; 2) the type of the biological tissue; or 3) a combination thereof. The herein disclosed chamber may have a volume of from about 1.0 cc to about 100,000 cc, for example, about 1.0 cc, about 5.0 cc, about 10 cc, about 50 cc, about 100 cc, about 500 cc, about 1,000 cc, about 5,000 cc, about 10,000 cc, about 50,000 cc, about 100,000 cc, or from any one of the above stated volumes to any other above stated volumes. The herein disclosed chamber may have a cross-sectional shape of a square, rectangle, trapezoid, triangle, hexagon, octagon, or circle. In some embodiments, the chamber is a syringe, test tube, centrifuge tube, falcon tube, Eppendorf tube, or a collection tube.

The herein disclosed cutting may be performed by any cutting device or cutter that is capable of cutting biological tissue that is fed to the cutter. The cutter is aligned with the herein disclosed conforming such that: 1) conformed tissue is positioned to be cut by the cutter; 2) tissue that is cut by the herein disclosed cutter is positioned to be conformed; and/or 3) tissue that is being conformed is positioned to be cut by the cutter. The cutting may be performed by one or more cutters. Optionally, the cutter is a movable cutter, for example, a rotating cutter, a linear-motion guillotine cutter, a vibrating cutter, an ultrasonic cutter, a waterjet cutter, a cutter that moves linearly, an oscillating blade including a serrated blade with or without an opposing fixed or counteracting blade, a plate, or a laser cutter A rotating cutter refers to one or more blades extending outward from a central axis of rotation. The rotating cutter may be actuated from either side of the cutter.

Aligning the cutter with the herein disclosed conforming may be performed by attaching the cutter to the herein disclosed chamber such that biological tissue within the chamber is fed along the direction of mincing to the cutter. One or more cutters may be placed on either side of the plate and/or within the plate between two portions of the plate positioned face to face. The cutter may be positioned at a distance from about 0 cm to about 10 cm from the herein disclosed plate, for example, about 0 cm, about 0.1 cm, about 0.2 cm, about 0.3 cm, about 0.4 cm, about 0.5 cm, about 0.6 cm, about 0.7 cm, about 0.8 cm, about 0.9 cm, about 1.0 cm, about 1.5 cm, about 2.0 cm, about 5.0 cm, about 7.0 cm, about 10 cm, or from any one of the above stated distances to any other above stated distances, or the herein disclosed cutter and the herein disclosed plate directly abut one another, i.e., are in direct contact with one another. In some embodiments, the cutter is attached at or near the end of the chamber on the emerging side of the plate. Optionally, in the embodiments where the cutter is attached at or near the end of the chamber on the emerging side of the plate, the cutter may be actuated from the emerging side of the plate. The herein disclosed chamber may adjust the velocity at which biological tissue is fed to the cutter by adjusting the velocity at which the member pushes biological tissue towards the cutter. The member may push biological tissue directly to the cutter or may push biological tissue directly to and through the plate before pushing the conformed tissue to the cutter.

The herein disclosed frequency of cutting may be adjusted by an actuator in communication with the cutter to adjust and control the number of cuts performed by the cutter over a period of time. In some embodiments, the cutter is a movable cutter and the actuator is a motor connected to the cutter, optionally by means of a shaft and/or one or more gears, that controls the speed of the cutter's cutting motion.

The herein disclosed cooperative conforming and cutting may be performed by cooperatively associating the herein described chamber, plate, and/or cutter. Cooperatively associating may refer to any physical or non-physical connection that allows two or more components to perform cooperatively. Optionally, a processor or controller in communication, for example electrical communication, with the chamber, plate and/or cutter may adjust one or more of the herein described conforming and/or cutting parameters to result in minced tissue fragments having a desired size and/or desired quantity of minced tissue fragments. Optionally, the processor is in communication with one or more actuators that physically perform the adjustments of the chamber, plate, and/or cutter. Optionally, a series of gears in communication with the chamber, plate, and/or cutter may adjust one or more of the herein described conforming and/or cutting parameters to result in minced tissue fragments having a desired size. Optionally, the conforming and cutting are performed cooperatively to control the size of minced tissue using Equation 2:

$$\text{Minced Tissue Size(e.g. minced tissue volume)} = \frac{\text{Velocity of tissue through the at least one hole} \times \text{cross-sectional area of the at least one hole}}{\text{Cutting Frequency}}. \quad \text{(Equation 2)}$$

Optionally, the conforming and cutting are performed cooperatively to control the size of minced tissue using Equation 3:

$$\text{Minced Tissue Size(e.g. minced tissue volume)} = \frac{\text{Velocity of tissue through the at least one hole} \times \text{cross-sectional area of the at least one hole}}{\text{Cutting Frequency} \times n(\text{number of holes})}. \quad \text{(Equation 3)}$$

With reference to Equations 2 and 3, the herein disclosed parameters of velocity of biological tissue along the direction of mincing through the at least one hole of the plate and fed to the cutter, the cross-sectional area of the at least one hole, the cutting frequency of the cutter, and/or the number of holes, are adjustable to result in minced tissue having a desired size, for example, from about 0.001 mm$^3$ to about 100,000 mm$^3$, for example, about 0.001 mm$^3$, about 0.005 mm$^3$, about 0.01 mm$^3$, about 0.1 mm$^3$, about 1.0 mm$^3$, about 10 mm$^3$, about 50 mm$^3$, about 100 mm$^3$, about 150 mm$^3$, about 200 mm$^3$, about 300 mm$^3$, about 350 mm$^3$, about 400 mm$^3$, about 500 mm$^3$, about 1,000 mm$^3$, about 10,000 mm$^3$, about 100,000 mm$^3$, or from any one of the above stated sizes to any other above stated sizes.

Optionally, the cooperatively associated chamber, plate, and/or cutter are automated to produce minced tissue fragments having a desired size(s) and/or desired quantity of minced tissue fragments. For example, a user may enter or set the desired minced tissue fragment size or sizes and the herein disclosed processor in conjunction with one or more actuators, automatically adjusts one or more parameters of the chamber, plate, and/or cutter to result in the desired minced tissue fragment size. Optionally, the user may enter or set the desired quantity of minced tissue fragments and the desired tissue fragment size(s), and the herein disclosed processor automatically adjusts one or more parameters of the chamber, plate, and/or cutter to result in the desired tissue quantity.

The herein disclosed devices or components that perform the herein disclosed methods may be made of material that is suitable for biomedical use, autoclavable, sterile, or any combination thereof, for example, stainless steel, titanium, tungsten carbide (blade), ceramic (blade), glass (chamber and containers), polymer (plastics, including polypropylene, polystyrene, acetal, polycarbonate, PETG, PET, and custom formulations) (chamber and containers.

The specification also describes a kit that includes one or more of the herein disclosed chamber, plate, cutter, actuators, processor, gears, and shaft. The components of the herein disclosed kit may be present in separate containers, or some or all of the components may be pre-combined and/or pre-assembled. Optionally, the kit comprises instructions for assembling the herein disclosed devices and/or for performing the herein disclosed methods.

Figure 2:
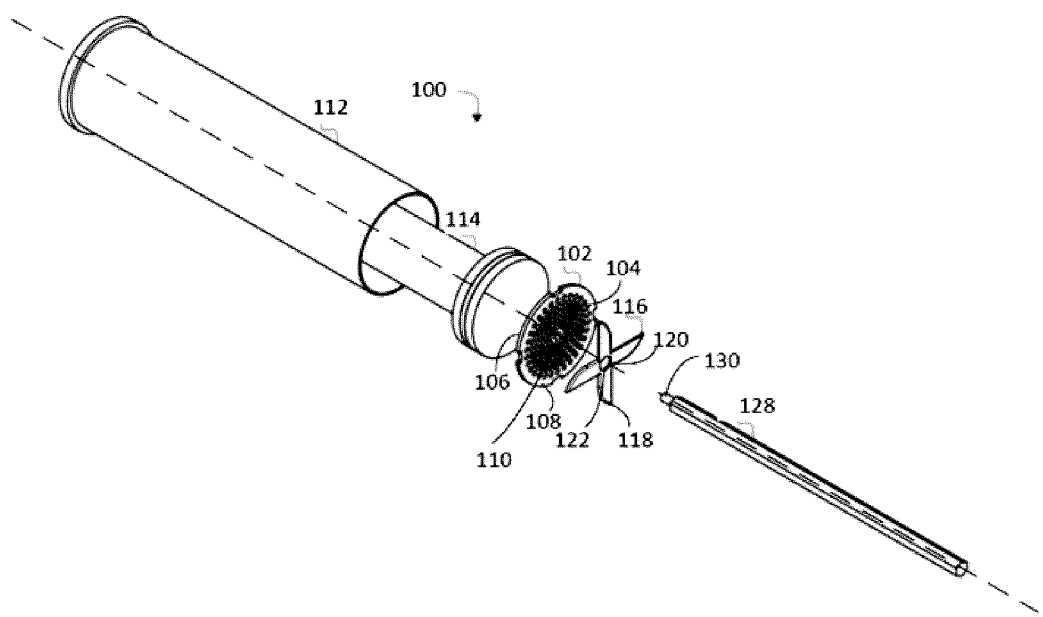
FIG. 2 is an exploded view of the mincing device illustrated in FIG. 1.

FIGS. 1 and 2 illustrate one example of a mincing device disclosed herein. The mincing device (100) comprises a conforming plate (102; also see FIG. 3) defining 130 holes (104) therethrough, and having a loading side (106) and an opposite emerging side (108). The conforming plate (102) also defines a central hole (110). The mincing device (100) also comprises a chamber (112) having a plunger (114) slidable within the chamber (112). The conforming plate (102) is coupled to the end of the chamber (112) with its loading side (106) aligned with the chamber (112) such that the plunger (114) is able to push biological tissue (not shown) within the chamber (112) towards and through the holes (104) of the conforming plate (102) in the direction of mincing (dashed line). The mincing device (100) also comprises a rotatable cutter (116; see FIG. 4) coupled to the emerging side (108) of the conforming plate. The cutter (116) comprising 4 blades (118) extending outward from a central axis of rotation (120). The cutter defines a central hole (122) having a hexagonal shape. The cutter (116) is aligned with the conforming plate (102) such that tissue that is pushed through the holes (104) of the conforming plate (102) is positioned to be cut by the cutter (116) (also see FIG. 5). The mincing device (100) is coupled to motors (124, 126). Motor (124) is coupled to chamber (112) and controls or adjusts the velocity that the plunger (114) pushes biological tissue along in the direction of mincing towards the conforming plate (102) and cutter (116). Motor (126) is coupled to the cutter (116) and conforming plate (102) by a shaft (128) and controls or adjusts the frequency the cutter (116) rotates and cuts biological tissue. A portion of the end (130) of the shaft (128) is sized to fit through the central hole (122) of the cutter (116) and engage the central hole (110) of the conforming plate (102), which helps align the cutter (116) with the conforming plate (102). The shaft (128) has a hexagonal shaped cross sectional area that corresponds to the hexagonal shape of the central hole (122) of the cutter (116) such that the shaft (128) fits inside the central hole (122) and physically engages the perimeter wall defining the central hole (122) when turned. The motors (124, 126) are automated and in communication with a processor (132) that controls and adjusts the motors (124, 126) to result in minced tissue fragments having a desired size (not shown). The processor (132) is configurable by the user to set the desired size of minced tissue fragments and/or the desired quantity of minced tissue fragments.

Figure 3:
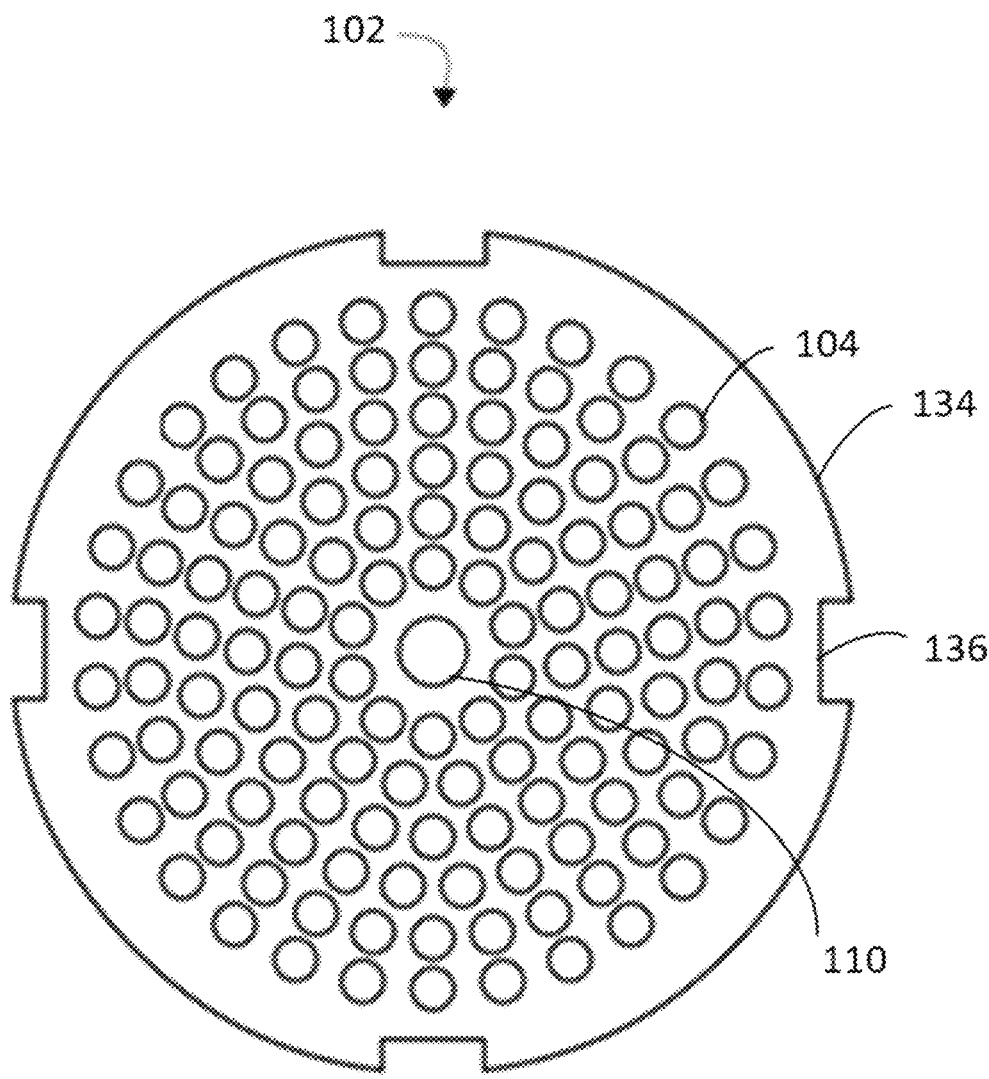
FIG. 3 is a side view of the conforming plate of the mincing device illustrated in FIG. 1.

FIG. 3 illustrates the conforming plate (102) from its emerging side (108) of the mincing device (100) illustrated in FIGS. 1 and 2. The conforming plate (102) defining holes (104) therethrough and having a rim portion (134) that defines 4 grooves (136) that are configured to releasably engage 4 corresponding latches (not shown) defined on the perimeter portion of the chamber (112).

Figure 4:
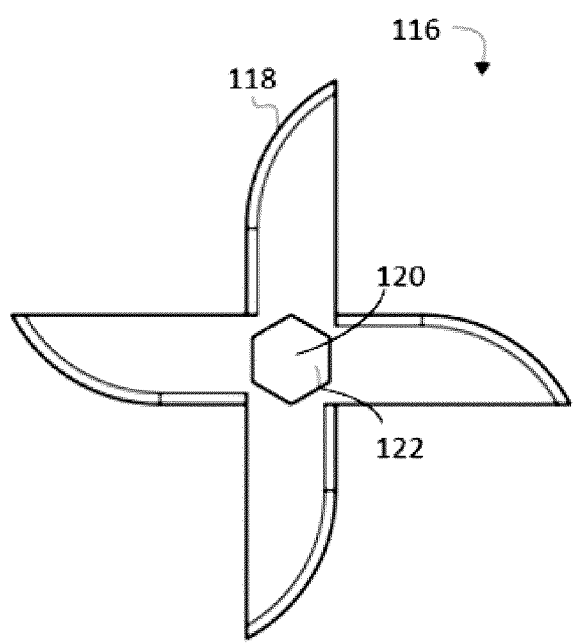
FIG. 4 is a side view of the cutter of the mincing device illustrated in FIG. 1.

FIG. 4 illustrates the cutter (116) of the mincing device (100) illustrated in FIGS. 1 and 2. The cutter (116) comprises 4 blades (118) extending outward from a central axis of rotation (120).

Figure 5:
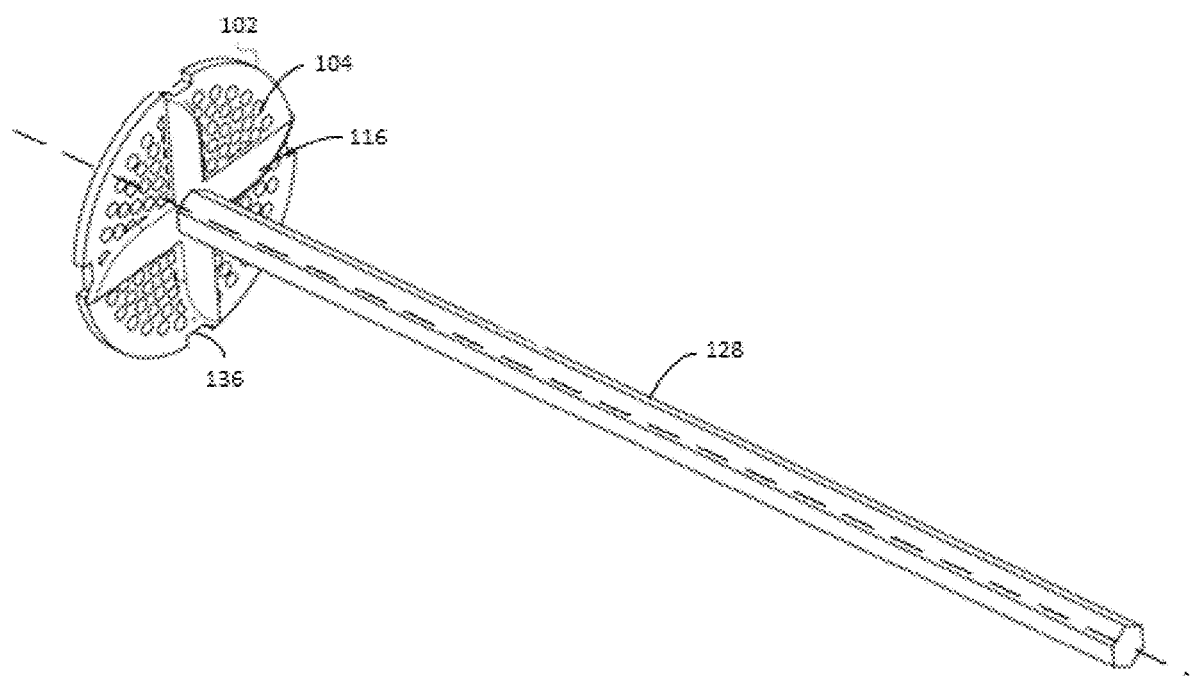
FIG. 5 is a side view of the conforming plate, cutter, and shaft of the mincing device illustrated in FIG. 1.

FIG. 5 illustrates the conforming plate (102), the cutter (116), and the shaft (128) of the mincing device (100) illustrated in FIGS. 1 and 2, coupled together.

In use, an operator configures the processor (132) to operate the mincing device (100) to produce minced biological fragments of a desired size and/or a desired quantity of minced tissue fragments. Depending on the desired size of minced fragments and/or the desired quantity of minced tissue fragments, the conforming plate (102) may be replaced with another conforming plate defining a different number, size, and/or shape of holes by decoupling conforming plate (102) from the chamber (112) and coupling the another conforming plate to the chamber (112). The biological tissue to be minced by the mincing device (100) is placed into the chamber (112) between the plunger (114) and the conforming plate (102). The processor (132) controls or adjusts motors (124, 126), which in turn control or adjust: 1) the velocity of the plunger (114) pushing the biological tissue within the chamber (112) along the direction of mincing towards and through the holes (104) of the conforming plate (102) and towards the cutter (116); and 2) the rotational speed of the cutter (116), based on the desired fragment size, using Equation 3. The processor also controls the length of time of mincing until the desired amount of minced tissue is produced. Minced tissue fragments may be collected for storage or use (not shown).

EXAMPLE

In one example using the herein disclosed device, the device was programmed using Equation 3 to produce 1 cc sized tissue fragments. Biological tissue was fed to a conforming plate at a velocity of about 1 cc of tissue per second through 1 hole defined by the plate, and cut with a frequency of about 1 Hz, producing about 1 cc sized tissue fragments. In a comparative example, the conforming plate defined 2 uniformly sized holes and the remaining conforming and cutting parameters were unchanged, producing tissue fragments having a size of about 0.5 cc.

In the preceding description, for purposes of explanation, numerous details are set forth in order to provide a thorough understanding of the examples. However, it will be apparent to one skilled in the art that these specific details are not required. Accordingly, what has been described is merely illustrative of the application of the described example and numerous modifications and variations are possible in light of the above teachings.

Since the above description provides examples, it will be appreciated that modifications and variations can be effected to the particular examples by those of skill in the art. Accordingly, the scope of the claims should not be limited by the particular examples set forth herein, but should be construed in a manner consistent with the specification as a whole.

The invention claimed is:

1. A device for mincing biological tissue, the device comprising:
a conforming plate defining at least one hole therethrough and having a loading side and an opposite emerging side, the conforming plate coupleable on the loading side with a tissue feeder to feed tissue through the at least one hole; and
a cutter configured to cut the tissue,
wherein the tissue feeder and the cutter cooperate to control the size of the minced tissue using at least one of the following equations:

$$\text{Minced Tissue Size(e.g. minced tissue volume)} = \frac{\text{Velocity of tissue through the at least one hole} \times \text{cross-sectional area of the at least one hole}}{\text{Cutting Frequency}}; \text{ and}$$

$$\text{Minced Tissue Size(e.g. minced tissue volume)} = \frac{\text{Velocity of tissue through the at least one hole} \times \text{cross-sectional area of the at least one hole}}{\text{Cutting Frequency} \times n(\text{number of holes})}.$$

2. The device of claim 1, wherein the biological tissue is epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof.

3. The device of claim 1, wherein the cutter is on the emerging side of the conforming plate.

4. The device of claim 1, wherein the cutter is from about 0 cm to about 10 cm from the conforming plate, or abutting the conforming plate.

5. The device of claim 1, wherein the cutter is a movable cutter, a rotating cutter, a linear-motion guillotine cutter, vibrating cutter, ultrasonic cutter, waterjet cutter, a cutter that moves linearly, an oscillating blade including a serrated blade with or without an opposing fixed or counteracting blade, a plate, or laser cutter.

6. The device of claim 5, wherein the movable cutter is actuated from the emerging side of the conforming plate.

7. The device of claim 1, wherein the cutter is configured to cut the tissue along a plane that is about perpendicular to the direction of the tissue being fed through the at least one hole.

8. The device of claim 1, wherein the cutter is configured to cut the tissue entirely along a cutting plane.

9. The device of claim 1, wherein the edge of the conforming plate defining the at least one hole is dull.

10. The device of claim 1, wherein the tissue feeder comprises a chamber, comprises a member, for example a plunger, movable within the chamber, the member configured for forcing the tissue through the at least one hole.

11. The device of claim 1, wherein the tissue feeder and/or the cutter is automated, and the tissue feeder and/or the cutter is in communication with a processor configured to control the size of the minced tissue.

12. The device of claim 1, wherein the device is made of material suitable for biomedical use, autoclavable, sterile, or any combination thereof.

13. A biological tissue mincing device for use with at least two actuators, the device comprising:
a conforming plate defining at least one hole therethrough and having a loading side and an opposite emerging side, the conforming plate coupleable on the loading side with a chamber to hold and feed biological tissue through the at least one hole; and
a cutter configured to cut the biological tissue,
wherein the chamber is cooperatively associated with the cutter to control the size of the minced biological tissue, and
wherein the chamber is coupleable with one of the at least two actuators, and wherein the cutter is coupleable with another of the at least two actuators, and
wherein the device is coupleable to a processor configured to control the size of the minced tissue using at least one of the following equations:

$$\text{Minced Tissue Size(e.g. minced tissue volume)} = \frac{\text{Velocity of tissue through the at least one hole} \times \text{cross-sectional area of the at least one hole}}{\text{Cutting Frequency}}; \text{ and}$$

$$\text{Minced Tissue Size(e.g. minced tissue volume)} = \frac{\text{Velocity of tissue through the at least one hole} \times \text{cross-sectional area of the at least one hole}}{\text{Cutting Frequency} \times n(\text{number of holes})}.$$

14. The tissue mincing device of claim 13, wherein the one actuator co-acts with the chamber and the another actuator co-acts with the cutter.

15. The tissue mincing device of claim 13, wherein the tissue is biological tissue, such as epithelial tissue, including dermal tissue, hepatocytes, endocrine glands; connective tissue, including bone, tendon, cartilage, adipose, and umbilical cord tissue; musculoskeletal tissue, including cardiac, smooth, and skeletal tissue; nervous tissue, including central nervous system, spinal cord and peripheral nerve tissue; or mixed tissue, including corneal, pancreatic, and renal parenchyma, hepatic tissue, kidney tissue, skin tissue, and any combination thereof.

16. The tissue mincing device of claim 13, wherein the cutter is on the emerging side of the conforming plate.

17. The tissue mincing device of claim 16, wherein the cutter is coupleable with the another actuator on the emerging side of the conforming plate.

18. The tissue mincing device of claim 13, wherein the cutter is from about 0 cm to about 10 cm from the conforming plate, or abutting the conforming plate.

19. The tissue mincing device of claim 13, wherein the cutter is a movable cutter, a rotating cutter, a linear-motion guillotine cutter, vibrating cutter, ultrasonic cutter, waterjet cutter, a cutter that moves linearly, an oscillating blade including a serrated blade with or without an opposing fixed or counteracting blade, a plate, or laser cutter.

20. The tissue mincing device of claim 13, wherein the cutter is configured to cut the tissue along a plane that is about perpendicular to the direction of the tissue being fed through the at least one hole.

21. The tissue mincing device of claim 13, wherein the cutter is configured to cut the tissue entirely along a cutting plane.

22. The tissue mincing device of claim 13, wherein the edge of the conforming plate defining the at least one hole is dull.

23. The tissue mincing device of claim 13, wherein the chamber is coupleable with a member, for example a plunger, movable within the chamber, the member configured for forcing the tissue through the at least one hole.

24. The tissue mincing device of claim 13, wherein the tissue feeder and/or the cutter is automated.

25. The tissue mincing device of claim 13, wherein the device is made of material suitable for biomedical use, autoclavable, sterile, or any combination thereof.

26. A kit comprising:
a chamber;
a conforming plate defining at least one hole therethrough and having a loading side and an opposite emerging side, the conforming plate coupleable on the loading side with the chamber to hold and feed biological tissue through the at least one hole; and
a cutter,
wherein the chamber is cooperatively associated with the cutter to control the size of minced biological tissue using at least one of the following equations:

$$\text{Minced Tissue Size (e.g. minced tissue volume)} = \frac{\text{Velocity of tissue in direction of mincing} \times \text{cross-sectional area of conformed tissue}}{\text{Cutting Frequency}};$$

$$\text{Minced Tissue Size (e.g. minced tissue volume)} = \frac{\text{Velocity of tissue through the at least one hole} \times \text{cross-sectional area of the at least one hole}}{\text{Cutting Frequency}}; \text{ and}$$

$$\text{Minced Tissue Size (e.g. minced tissue volume)} = \frac{\text{Velocity of tissue through the at least one hole} \times \text{cross-sectional area of the at least one hole}}{\text{Cutting Frequency} \times n(\text{number of holes})}.$$

27. A device for mincing biological tissue, the device comprising:
a conforming plate defining at least one hole therethrough and having a loading side and an opposite emerging side, the conforming plate coupleable on the loading side with a tissue feeder to feed tissue through the at least one hole; and
a moveable cutter configured to cut the tissue, the moveable cutter actuated from the emerging side of the conforming plate, wherein the tissue feeder and the cutter cooperate to control the size of the minced tissue.

* * * * *